United States Patent
Hellenbrand et al.

(10) Patent No.: US 9,984,353 B2
(45) Date of Patent: May 29, 2018

(54) METHOD FOR DETECTING INCORRECT STORAGE OF MEDICATION PACKAGES

(71) Applicant: CareFusion Germany 326 GmbH, Kelberg (DE)

(72) Inventors: Christoph Hellenbrand, Kaifenheim (DE); Dennis Reif, Kaisersesch (DE); Andreas Klapperich, Rieden (DE)

(73) Assignee: CAREFUSION GERMANY 326 GMBH, Kelberg (DE)

( * ) Notice: Subject to any disclaimer, the term of this patent is extended or adjusted under 35 U.S.C. 154(b) by 665 days.

(21) Appl. No.: 14/380,691

(22) PCT Filed: Jan. 24, 2013

(86) PCT No.: PCT/EP2013/051386
§ 371 (c)(1),
(2) Date: Aug. 22, 2014

(87) PCT Pub. No.: WO2013/124115
PCT Pub. Date: Aug. 29, 2013

(65) Prior Publication Data
US 2015/0012293 A1    Jan. 8, 2015

(30) Foreign Application Priority Data
Feb. 22, 2012 (EP) ................... 12156529

(51) Int. Cl.
*G06Q 10/08* (2012.01)
*B65G 1/137* (2006.01)
(Continued)

(52) U.S. Cl.
CPC ......... *G06Q 10/087* (2013.01); *B65G 1/0421* (2013.01); *B65G 1/1371* (2013.01);
(Continued)

(58) Field of Classification Search
CPC .. G06Q 10/087; G06Q 20/203; B65G 1/1371; B65G 2203/041; B65G 1/0421;
(Continued)

(56) References Cited

U.S. PATENT DOCUMENTS 3,651,478 A  *  3/1972  Shandlay ............. B65G 1/1371
                                                     705/28
4,673,932 A  *  6/1987  Ekchian ................ G01S 13/753
                                                     235/385
(Continued)

FOREIGN PATENT DOCUMENTS

CN       201506600 U    6/2010
DE    202004004292 U1   5/2004
(Continued)

*Primary Examiner* — Christopher Stanford
(74) *Attorney, Agent, or Firm* — McDermott Will & Emery LLP (57) ABSTRACT

The invention relates to a method for detecting incorrect storage of medicament packages in a pharmacy order-picking device. Such incorrect storage can occur in the event that manual removal of medicament packages becomes necessary due to a malfunction. The pharmacy order-picking device comprises a series of shelves comprising a plurality of shelf compartments and at least one movable operating device in front of the row of shelves, wherein the operating device has a gripping device as well as a sensor. In order to detect incorrect storage, shelf compartments with potential incorrect storage of medicament packages are detected; the operating device is moved to a prescribed shelf position if a shelf compartment is detected; with the sensor switched on, the operating device moves across a detected shelf compartment in a horizontal direction, detects the storage depths at various X positions using the sensor and creates a virtual image of the actual situation on the basis of the detected storage depths; the image of the actual situation is then compared with a target image of the shelf compartment.

20 Claims, 6 Drawing Sheets (51) Int. Cl.
  *G06F 19/00* (2018.01)
  *G06Q 20/20* (2012.01)
  *B65G 47/90* (2006.01)
  *B65G 1/04* (2006.01)

(52) U.S. Cl.
  CPC ........ *G06F 19/3456* (2013.01); *B65G 1/0407* (2013.01); *B65G 47/90* (2013.01); *B65G 2203/041* (2013.01); *G06Q 10/08* (2013.01); *G06Q 20/203* (2013.01)

(58) Field of Classification Search
  CPC .. B65G 47/90; B65G 1/0407; G06K 2209/19; G07F 17/0092; G07F 11/165
  See application file for complete search history.

(56) References Cited

U.S. PATENT DOCUMENTS

| | | | | |
|---|---|---|---|---|
| 5,487,579 | A * | 1/1996 | Woodruff | G11B 23/0236 294/115 |
| 5,671,362 | A * | 9/1997 | Cowe | G06Q 10/087 340/5.92 |
| 7,177,459 | B1 * | 2/2007 | Watanabe | B25J 9/1697 382/151 |
| 8,577,136 | B1 * | 11/2013 | Ascher | G06Q 10/087 382/165 |
| 2002/0173875 | A1 * | 11/2002 | Wallace | G06F 19/322 700/242 |
| 2007/0069867 | A1 * | 3/2007 | Fleisch | G06Q 10/087 340/309.16 |
| 2008/0077510 | A1 * | 3/2008 | Dielemans | G06Q 10/087 705/28 |
| 2009/0063307 | A1 * | 3/2009 | Groenovelt | G06Q 10/087 705/28 |
| 2009/0204512 | A1 * | 8/2009 | Connell, II | G06Q 10/087 705/28 |
| 2010/0039513 | A1 * | 2/2010 | Glickman | G06K 9/00 348/143 |
| 2010/0300041 | A1 * | 12/2010 | Kim | G07F 11/165 53/281 |

FOREIGN PATENT DOCUMENTS

| | | |
|---|---|---|
| EP | 1627830 A1 | 2/2006 |
| JP | H-0624528 A | 2/1994 |

* cited by examiner

METHOD FOR DETECTING INCORRECT STORAGE OF MEDICATION PACKAGES

CROSS-REFERENCE TO RELATED APPLICATION

This application is the U.S. National Phase under 35 U.S.C. § 371 of International Application No. PCT/EP2013/051386, filed on Jan. 24, 2013, which claims the benefit of EP 12156529.5, filed Feb. 22, 2012. The entire contents of these applications are incorporated by reference herein.

BACKGROUND

In some pharmacy order-picking devices, a large number of various and differently dimensioned medication packages (piece goods) may be stored chaotically and in a space-optimized manner on elongated shelf bases. These shelf bases form, together with the shelf walls, the shelf compartments, wherein a large number of medication packages is stored per shelf compartment, or per shelf base.

During the storage of medication packages in a shelf compartment, each medication package may be assigned a storage space and this, with other items of information on a medication package, is stored in a control unit. With the aid of the items of information stored in the control unit, the medication package can be accessed using the operating device for a retrieval or relocation which is possibly to be performed of a specific medication package.

SUMMARY

The present disclosure relates to a method for operating a pharmacy order-picking device. In particular, the present disclosure relates to a method for ascertaining, and if desired, remedying incorrect storage of medication packages in a pharmacy order-picking device having at least one row of shelves having in each case a plurality of shelf bases extending in a horizontal direction (X axis) and a plurality of shelf walls extending in a vertical direction, wherein the shelf bases and shelf walls form a plurality of shelf compartments, at least one operating device which is horizontally and vertically movable in front of the row of shelves, wherein the operating device includes a gripping device for storing and/or retrieving medication packages on or from, respectively, the shelf bases, and a sensor, and a control unit which is coupled to the operating device.

The storage or retrieval typically runs completely automatically, without a user having to intervene, except by inputting various instructions. However, if disturbances occur in the pharmacy order-picking device, for example, a power failure, or a mechanical or electrical defect, a user may perform the retrieval of the required medication packages manually, wherein the user is guided to the appropriate shelf compartment, at which the medication package to be removed is stored, via a user guide of the pharmacy order-picking device.

Diverse errors can occur during the manual retrieval; for example, the wrong medication package can be removed, adjacent medication packages can be shifted during the removal, or a medication package which lies in the path of that to be removed can be relocated into another shelf compartment and forgotten therein. This has the result that incorrect storage of medication packages can occur in the manually operated shelf compartment (and possibly further compartments, if medication packages were relocated). When the pharmacy order-picking device is changed back to fully automatic operation after the disturbance is remedied, depending on the type of the incorrect storage, medication packages may not be removable or there may be a delay in removing medication packages from shelf compartments having incorrect storage.

It is therefore the object of the present disclosure to provide a method for ascertaining and possibly remedying incorrect storage of medication packages in a pharmacy order-picking device.

The pharmacy order-picking device used in a method described herein includes at least one row of shelves having in each case a plurality of shelf bases extending in a horizontal direction (X direction, X axis) and a plurality of shelf walls extending in a vertical direction, wherein the shelf bases and the shelf walls form a plurality of shelf compartments, which are typically elongated (in the X direction). Furthermore, the pharmacy order-picking device includes an operating device, which is movable horizontally and vertically in front of the row of shelves, and a control unit coupled to the operating device, wherein the operating device itself includes a gripping device for storing and/or retrieving medication packages on or from the shelf base, and a sensor.

In the scope of this application, the term "medication package" is to be interpreted as "at least one medication package"; it also includes the retrieval of a plurality of (successively) stored medication packages.

The sensor may be a distance sensor having a unit for emitting measurement beams and for receiving measurement beams, wherein the two units can be combined into one unit. During the distance determination, the sensor can detect the direction or runtime of an actively emitted signal which is reflected on a surface (of a medication package or a component of the pharmacy order-picking device). The distance determination can also be carried out capacitively or on the basis of the parallax or a stereo image of an electronic camera.

In pharmacy order-picking devices, laser distance sensors, which operate according to the principle of laser triangulation, are typical. In this case, a laser beam is oriented onto a surface (see above) and observed using the receiving unit (for example, camera, photodiode, diode array) located in the sensor. If the distance of the surface from the sensor changes, the angle at which the light spot is observed, and therefore the position of the image on the receiver of the receiving unit, also changes. For example, if a diode array is used, the diode which detects the reflected light beam changes with the distance. The distance of the surface from the sensor can be calculated from the position change.

For reasons of cost, the distance measurement is generally carried out as a "single-point measurement." That is, the measurement beam is emitted at a constant angle and is incident, without movement of the operating device, on the same point (single point). The reflected beam may be detected using a diode array.

The distance measurement can be carried out in this case so that only the detection at a specific diode (or a diode bundle) of the array is differentiated from the detection outside this diode or the diode bundle. The distance measurement then only recognizes two states ("binary distance measurement" hereafter).

To detect incorrect storage, shelf compartments having possible incorrect storage of medication packages are ascertained, for example, in that they are marked as such by a user. For example, in the case of a manual removal when medication packages may be shifted, every shelf compartment in which a manual engagement was made should be marked. The operating device is then moved to a predefined shelf position at an ascertained shelf compartment. This shelf position may be the left or right corner (in relation to the corner of shelf space/shelf wall).

Using the operating device, with activated sensor, the shelf compartment is traveled in the horizontal direction (X axis), beginning at the approached shelf position, and the storage depth is ascertained at various X positions using the sensor. To what extent and at which, or at how many positions, the storage depth is determined results from the type of the sensor used and therefore the manner in which the storage depth is determined. For example, if a sensor for single-point measurement is used, the shelf compartment may be traveled completely in the horizontal direction, at least in the region in which an incorrect storage can occur. In another example, if a sensor having a camera is used, it may be sufficient to ascertain the storage depths at a number of X positions dependent on the width of the shelf compartment, wherein then point storage depths are not determined, but rather the storage depth is determined for an entire section.

A virtual actual image of the shelf compartment is prepared on the basis of the ascertained storage depths, wherein the data ascertained by the sensor are used to prepare this actual image. The actual image ($AB_I$) thus prepared is compared to a target image ($AB_S$) of the shelf compartment and deviations between the target image and the actual image are analyzed. If multiple shelf compartments are marked as shelf compartments having possible incorrect storage, this operation is repeated for the remaining shelf compartments.

An incorrect storage in the shelf compartment may be concluded on the basis of the analysis of the deviations between the target image of a shelf compartment and the actual image; for this purpose, the storage depth, which can be ascertained using the sensor, at various X positions of a shelf compartment is used. If a medication package is stored at an arbitrary X position (typically in contact with the shelf rear wall), the storage depth is different than if no or multiple medication packages were stored. The storage depth expected for a specific X position is known, since the dimensions thereof were stored with storage of each medication package; these items of information are absolutely necessary for the space-optimized storage of the medication packages.

In a method described herein, only known items of information are thus used; storage of additional items of information is not necessary. The method may be carried out using the "typical" components, installation of additional components is not necessary. The method described herein may therefore be implemented cost-effectively and rapidly.

Shelf compartments having possible incorrect storage can be ascertained, in that they are marked as such by a user or automatically after a manual retrieval of medication packages. A corresponding marking of shelf compartments restricts the number of the compartments to be examined, and the processing time of the method decreases.

After a disturbance of the pharmacy order-picking device, shelf compartments affected by the disturbance (which may be all of the shelf compartments) can be marked as shelf compartments having possible incorrect storage. All of the storage compartments may be marked if retrievals or storages may have occurred, but were not noted in the theoretical inventory (for example, as a result of a malfunction of the operating device or the identification unit). Marking all shelf compartments for an examination is also advisable if an "inventory" is to be carried out.

The target image of a shelf compartment can be calculated, in a preferred embodiment of the disclosure, on the basis of the target occupation of the shelf compartment for the comparison to the prepared actual image. During the storage of medication packages, the control unit stores all items of information, (inter alia, placement space, dimensions) which are necessary for the calculation of a target image. The calculation of the target image "on-demand" has the advantage that the required computing power is first requested when it is actually required. Also, the target image of the shelf compartment can be prepared or updated during the storage and/or retrieval of medication packages in or from, respectively, the shelf compartment, stored in a memory of the control unit, and loaded from a memory of the control unit for the comparison. This embodiment has the advantage that the recognition can be carried out particularly rapidly, since the target image does not have to be calculated, but rather is already present in the memory of the control unit.

For example, if the automatic retrieval is not possible in the event of a system failure of the operating device, medication packages may possibly be retrieved manually by the user. The user may be guided, for example, via a corresponding menu guide to the shelf compartment and the storage space of the medication package. In the case of the automatic retrieval, the medication package is automatically erased from the theoretical inventory and the storage space is released for renewed storage (the storage space was blocked for further storage during storage of the retrieved medication package). Because of time pressure, in the event of a manual retrieval, the user may forget receipt for the medication package; the theoretical inventory and the theoretically free storage space then deviate from the actual ones. To avoid this, in a preferred embodiment, if the analysis of the deviations between the target image and the actual image has the result that a medication package is missing in the shelf compartment, it is erased from a theoretical inventory stored in the storage unit.

In the case of manual removal, it can also occur that an operator may first relocate another medication package to retrieve a specific medication package and this package then remains in the shelf compartment into which it was relocated. As a result, one medication package in excess is located in this shelf compartment, which is not recorded in the theoretical inventory for this shelf compartment. In a preferred embodiment, if the analysis of the deviations between the target image and the actual image has the result that a medication package which is not recorded in the theoretical inventory is stored in the shelf compartment, it is retrieved or identified and stored again.

In the case of the manual removal of a package, as a result of the proximity of the packages to one another, it can occur that one or more adjacent medication packages are shifted. That is, these are no longer located as is expected according to the storage. In the scope of this application, the term "displaced" is to comprise not only medication packages moved in parallel to an axis, but rather also those which are only or also pivoted (about the central axis on a shelf base).

On the basis of the incorrect storage of the medication package(s), in a preferred exemplary embodiment, it is then checked whether the shifted medication package can be retrieved using the gripping device. If this is possible, which is dependent in particular on the inclination of the medication package and the package density on the shelf space, this medication package is retrieved and stored again.

If a retrieval is not possible using the gripping device (for example, as a result of the excessively small spacing to adjacent medication packages), it is first checked whether the medication package can be unambiguously assigned to a theoretically present medication package. If this is the case and it is known which package it is, but it cannot be retrieved without disturbing the adjacent medication packages, in one embodiment, the surrounding medication packages are retrieved (except for the medication package having incorrect storage), which can be accessed without disturbing the adjacent packages, and then the remaining medication package is retrieved and stored again.

If the medication package cannot be unambiguously assigned to a theoretically present medication package, in one embodiment, it is ascertained (on the basis of the actual image, the target image, and the theoretical occupation) which adjacent medication packages can be assigned to theoretically present medication packages (and can also be retrieved). Then, all those medication packages which can be assigned to theoretically present medication packages are retrieved. Subsequently, the remaining medication packages are retrieved, identified again, and then stored again. In this exemplary embodiment, it is necessary, as a result of the lack of a possibility of assigning shifted medication packages, to identify them before the renewed storage. In all of the above-mentioned exemplary embodiments, the retrieval, relocation, and further storage are accompanied by a continuous update of the theoretical occupation.

For example, if during the analysis of the deviations, it is determined that medication packages cannot be retrieved using the gripping device, the user is informed accordingly and prompted to perform manual removal.

In a preferred exemplary embodiment, the shelf compartment is checked once again after the correction of the incorrect storage, and in the event of a positive result of this check (all medication packages are stored at the theoretically provided storage space), the shelf compartment is released for further storage/retrieval. For this purpose, the shelf compartment is traveled once again completely in the horizontal direction (X axis) and the storage depth is ascertained at various X positions using the sensor. A virtual actual image of the shelf compartment is prepared on the basis of the ascertained storage depths and the prepared actual image is compared to a target image of the shelf compartment and deviations between the target image and the actual image are analyzed. If the shelf compartment was previously blocked for a further storage, it is released again for storage in the event of a positive analysis.

A method described herein will be described in greater detail hereafter on the basis of preferred embodiments illustrated in the drawings. In the figures of the drawings:

BRIEF DESCRIPTION OF THE DRAWINGS

FIG. 2b illustrates a front view of the shelf compartment shown in FIG. 2a.

FIG. 3b illustrates a comparison between the target image according to FIG. 2a and the actual image of the shelf compartment shown in FIG. 3a.

FIG. 4b illustrates a comparison between the target image according to FIG. 2a and the actual image of the shelf compartment shown in FIG. 4a.

FIG. 5b illustrates a comparison between the target image according to FIG. 2a and the actual image of the shelf compartment shown in FIG. 5a.

FIG. 6b illustrates a comparison between the target image according to FIG. 2a and the actual image of the shelf compartment shown in FIG. 6a.

DETAILED DESCRIPTION

Figure 1:
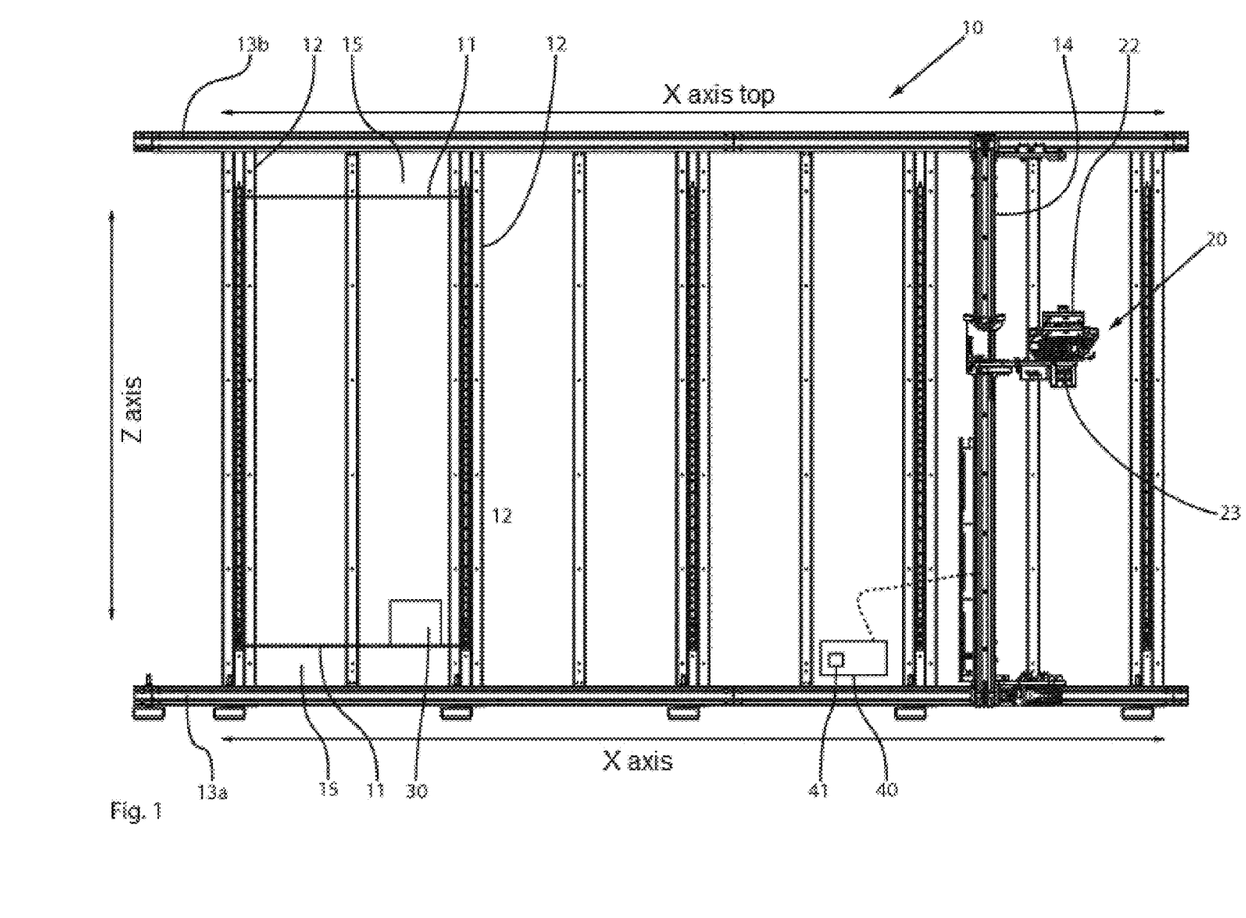
FIG. 1 illustrates a side view of a row of shelves of a pharmacy order-picking device.

FIG. 1 illustrates a side view of a row of shelves 10 of a pharmacy order-picking device. The row of shelves 10 includes a plurality of vertical shelf walls 12 and a plurality of horizontal shelf bases 11, which are typically glass bases or bases made of a comparable material. The shelf bases 11 and the shelf walls 12 form in each case shelf compartments 15, in which the medication packages are stored, wherein only one medication package 30 is shown as an example in FIG. 1.

An operating device 20, which includes a sensor 23 and a gripping device 22, on a guide, which includes two horizontal guide rails 13a, 13b and one vertical guide rail 14, is movable in front of the row of shelves 10. The operating device 20 is coupled to a control unit 40, which has a memory 41, inter alia.

Figure 2A:
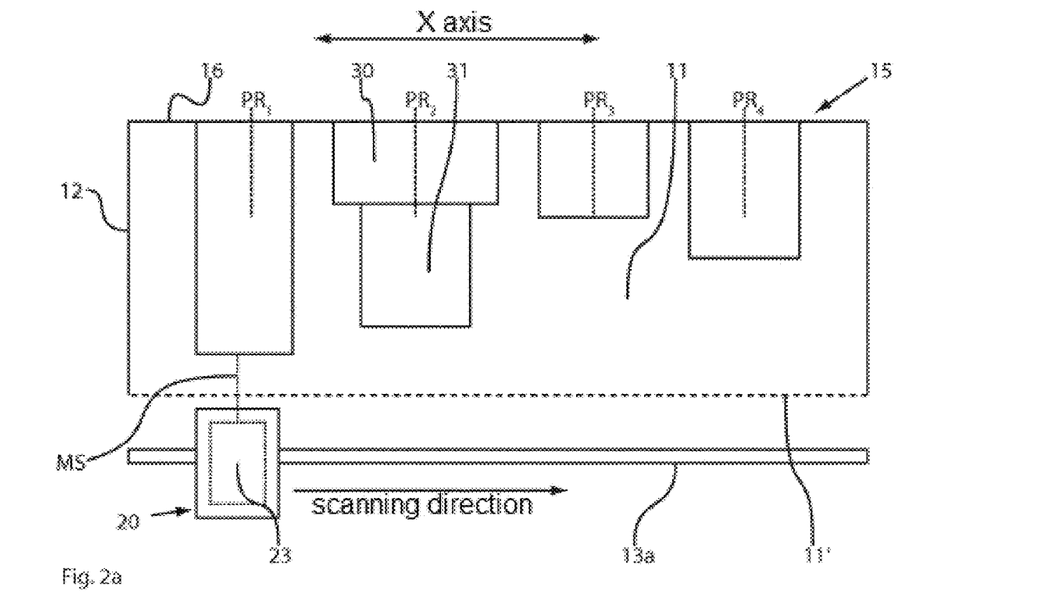
FIG. 2a illustrates a top view of a schematically illustrated shelf compartment and a schematic illustration of the operating device, which is movable in front of the shelf compartment.

FIG. 2a illustrates a top view of a shelf compartment 15, which is only schematically illustrated, and which is formed by two shelf walls 12, a shelf rear wall 16, and the shelf base 11. A plurality of such rows of shelves (or shelf compartments) is arranged per row of shelves 10 in the pharmacy order-picking device. The dimensions of the individual compartments are dependent on the overall construction of the pharmacy order-picking device. Because of the type of the storage and the fully automatic storage and retrieval, the shelf compartments are typically elongated, wherein the longitudinal axis corresponds to the X axis of the pharmacy order-picking device. The medication packages are in turn stored in rows in the shelf compartments, wherein multiple medication packages can also be stored per row.

In the exemplary embodiment shown, four rows of packages $PR_1$-$PR_4$ are present in the shelf compartment 15, wherein the row of packages $PR_2$ includes two medication packages 31, 31.

The medication packages are typically stored, if only one medication package is arranged per row of packages, flush on the shelf rear wall 16. If multiple medication packages are stored in one row of packages, these medication packages are stored flush on one another.

To ascertain incorrect storage in a shelf compartment, it is marked as a shelf compartment having possible incorrect storage. For example, a user may mark the shelf compartment as having possible incorrect storage, or the shelf may be automatically marked after a manual retrieval. The operating device 20, which is not shown to scale in FIG. 2, is moved to a predefined shelf position at the ascertained shelf compartment. This shelf position may lie on the outside on the left or right, to be able to carry out the method as rapidly as possible (if the single point measurement is used, for which the description of the method is referred to).

With activated sensor 23, the shelf compartment is then completely traveled in the horizontal direction using the operating device. The movement direction is unimportant in this case. The travel of the shelf can also start in the middle, for example, wherein further paths are then to be covered, however. It is only important that the shelf is completely traveled in the X direction using the sensor and the storage depth is ascertained at various X positions in this case. It is unimportant for the method according to the disclosure how the storage depths are detected in detail and this does not require more detailed description; it is important that the distance from sensor to medication package/shelf rear wall is ascertained at a plurality of points.

The sensor is to be aligned in this case, so that it is not oriented on to the end side of the shelf base or over several of the medication packages, but rather can detect the end face of all medication packages stored in the shelf compartment, insofar as this is possible as a result of their arrangement in front of or behind one another.

Figure 2B:
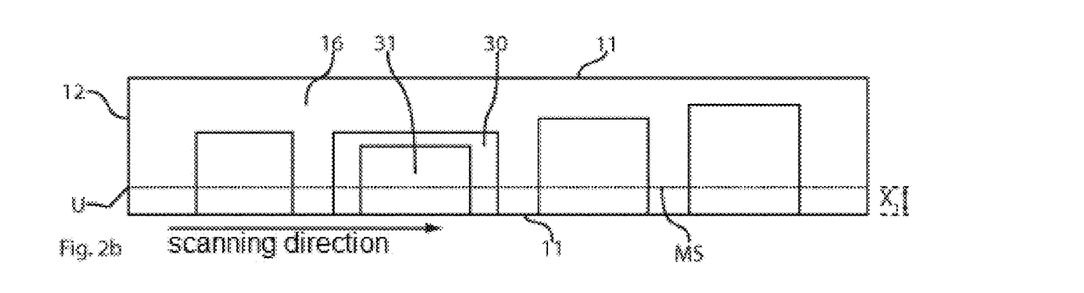

FIG. 2b illustrates a front view of the shelf compartment 15 shown in FIG. 2a, wherein the path of the measurement beam during the travel along the shelf compartment is illustrated using the dotted line. The point of incidence of the measurement beam is selected (distance $X_1$ to the shelf base 11) so that the end faces of all "visible" medication packages can be detected. The starting point during the generation of the depth profile or distance profile is indicated with "U".

Figure 2C:
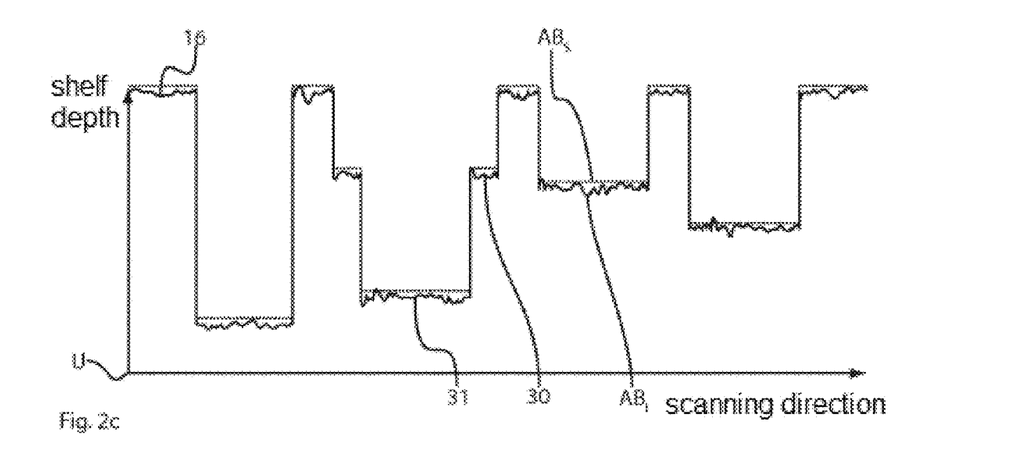
FIG. 2c illustrates the actual image ascertained using the sensor of the shelf compartment illustrated in FIG. 2a in comparison to the calculated target image.

During the travel along the shelf compartment in the X direction, on the basis of the X positions and the storage depths, an actual image $AB_I$ of the shelf compartment is prepared, which reproduces the depth profile and which is schematically shown in FIG. 2c as a jagged line (the jagged line is to indicate measurement uncertainties). In dependence on the width and the type of the stored medication packages, a continuous measurement, as shown in FIG. 2b, does not have to be carried out. Rather, it may be sufficient for the distance measurement only to be carried out at points. For example, the point intervals may be one measurement per millimeter. Furthermore, the target image $AB_S$ of the theoretical occupation of the shelf compartment 15, determined from the stored items of information about the individual medication packages, is illustrated in FIG. 3c. As can be recognized, the actual image, except for deviations based on measurement uncertainties or measurement variations, essentially corresponds to the target image.

Figure 3A:
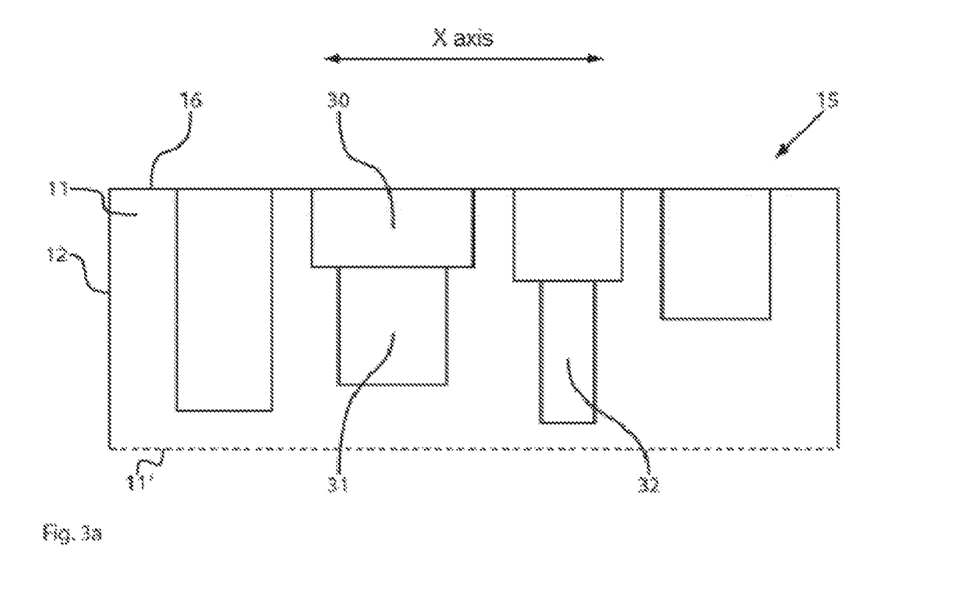
FIG. 3a illustrates a top view of a shelf compartment having incorrect occupation.

FIG. 3a illustrates the shelf compartment 15 having an occupation, in which, in comparison to the shelf occupation from FIG. 2a, additionally one medication package 32 is arranged in the row of packages $PK_3$.

Figure 3B:
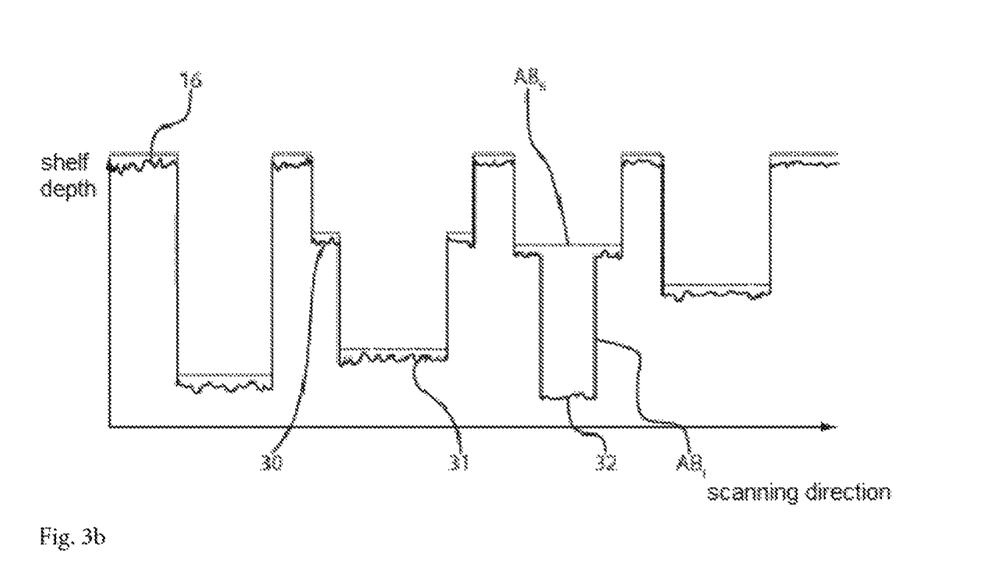

FIG. 3b illustrates (as a jagged line), the virtual actual image $AB_I$ of the shelf compartment 15 occupied according to FIG. 3a, which is obtained on the basis of the ascertained storage depths. Furthermore, the target image $AB_S$ of the occupation of the shelf compartment shown in FIG. 2a is illustrated in FIG. 3b (as a dotted line).

In a method described herein, the target image and the actual image are compared to one another and deviations between the target image and the actual image are analyzed. The comparison has the result in the present case that the actual image has an area in the row of packages $PK_3$, which should not be present according to the target image. Based on analysis of this deviation, it is determined that a medication package is stored in the shelf compartment 15, which should not be present there according to the theoretical occupation of the shelf compartment.

This medication package 32 is retrieved and then optionally newly identified and stored to reproduce the theoretical occupation of the shelf compartment 15.

Figure 4A:
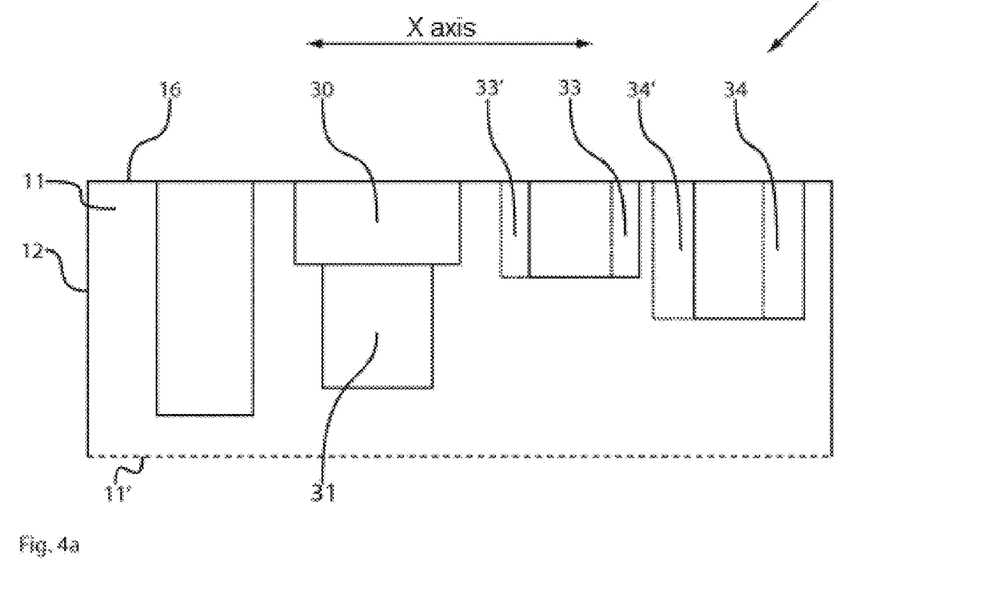
FIG. 4a illustrates a top view of a shelf compartment having incorrect occupation.

FIG. 4a illustrates the shelf compartment 15 having an occupation in which, in comparison to the compartment occupation from FIG. 2a, medication packages 33, 34 in rows of packages $PK_3$ and $PK_4$ are shifted (the original storage spaces are indicated with 33' and 34').

Figure 4B:
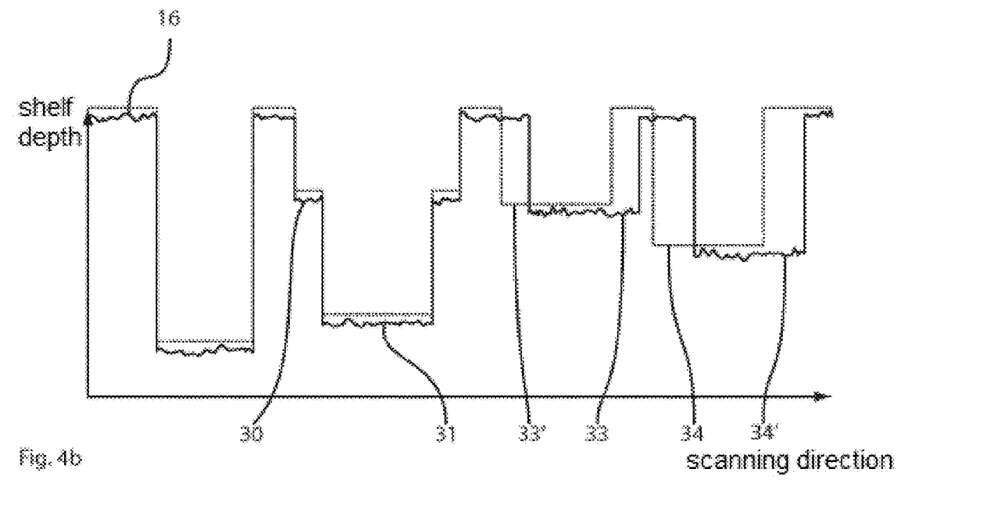

FIG. 4b illustrates (as a jagged line), the virtual actual image $AB_I$ of the shelf compartment 15 occupied according to FIG. 4a, which was obtained on the basis of the ascertained storage depths. Furthermore, the target image $AB_S$ of the occupation of the shelf compartment shown in FIG. 2a is illustrated in FIG. 4b (as a dotted line).

Based on analysis of the comparison of target image/ actual image, it is determined that two medication packages 33, 34 are shifted. Furthermore, it is determined that the medication packages 34 are shifted such that (specifically by the same amount to the "right") they can still be gripped using the gripping device 22. The medication packages 33, 34 are accordingly moved using the gripping device back to their storage space corresponding to the theoretical state. For this purpose, the medication packages can be shifted on the shelf base 11 or retrieved and stored again.

Figure 5A:
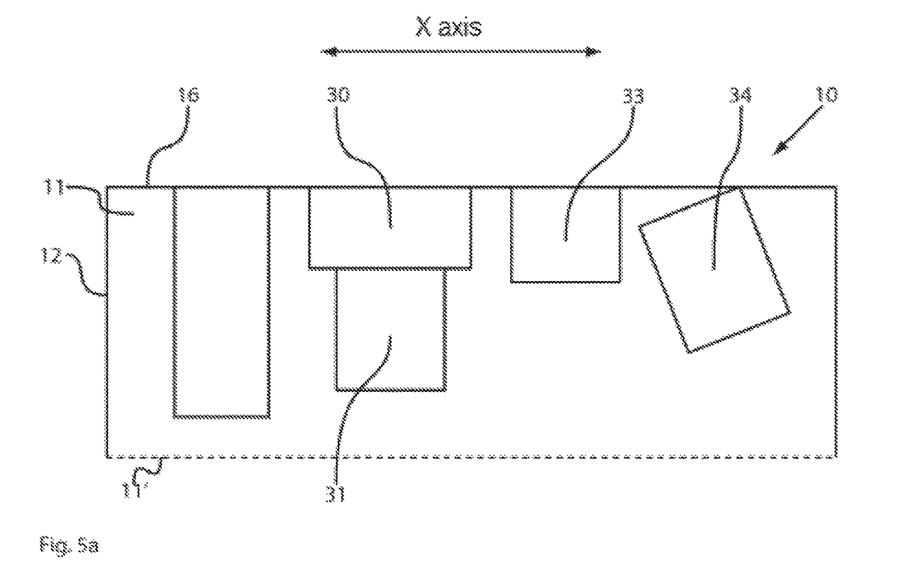
FIG. 5a illustrates a top view of a shelf compartment having incorrect occupation.

FIG. 5a illustrates the shelf compartment 15 having an occupation in which, in comparison to the compartment occupation from FIG. 2a, medication package 34 in the row of packages $PK_4$ is shifted, and specifically such that the medication package no longer presses against the shelf rear wall 16.

Figure 5B:
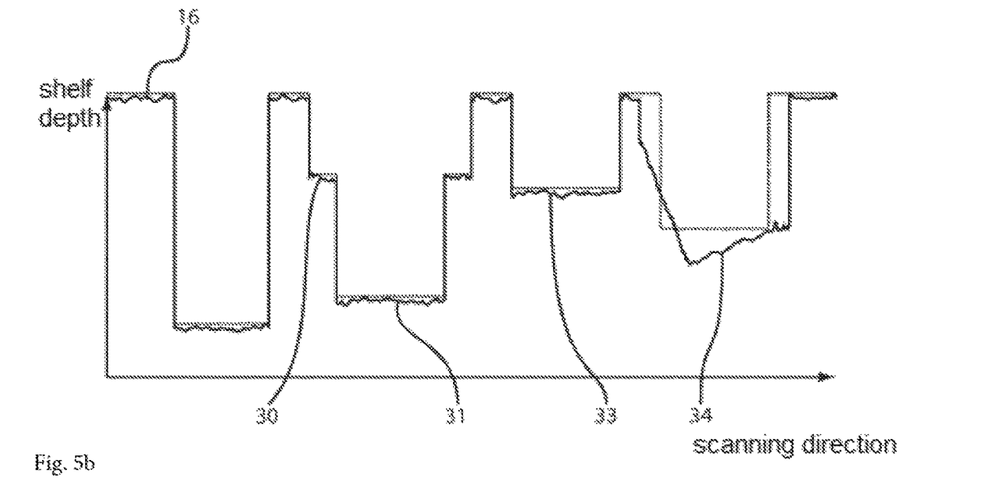

FIG. 5b illustrates (as a jagged line) the virtual actual image $AB_I$ of the shelf compartment 15 occupied according to FIG. 5a, which is prepared on the basis of the ascertained storage depths. Furthermore, the target image $AB_S$ of the occupation of the shelf compartment shown in FIG. 2a is illustrated in FIG. 5b (as a dotted line).

Based on analysis of the comparison of target image/ actual image, it is determined that the medication package 34 is shifted. Furthermore, it is determined that the medication package 34, in spite of the shifting, can be assigned to a medication package which is theoretically present in the inventory, and it can still be grasped using the gripping device 22 (there is sufficient distance between the medication package 34 and the adjacent medication package or shelf wall both on the left and also on the right to carry out a retrieval using the gripping device). The medication package 34 is retrieved using the gripping device and stored again. Merely displacing it on the shelf base is not possible as a result of the inclination.

Figure 6A:
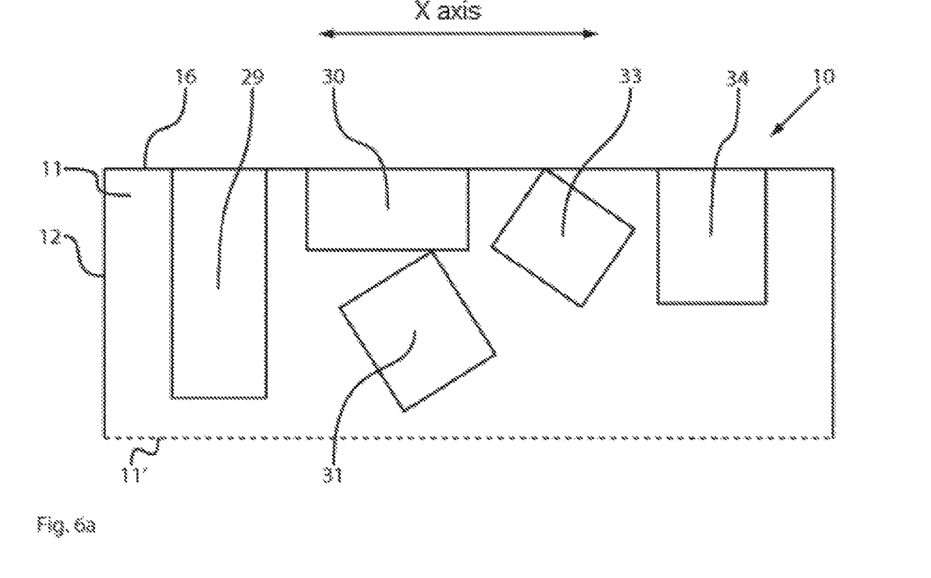
FIG. 6a illustrates a top view of a shelf compartment having incorrect occupation.

FIG. 6a illustrates the shelf compartment 15 having an occupation in which, in comparison to the shelf occupation from FIG. 2a, two medication packages 31, 34 in the rows of packages $PK_2$ and $PK_3$ are shifted or pivoted.

Figure 6B:
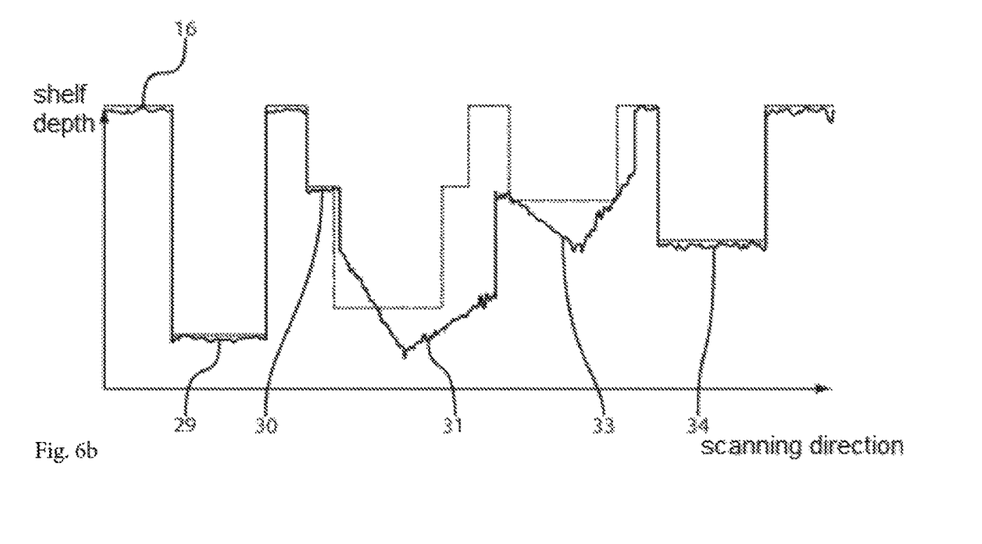

FIG. 6b illustrates (as a jagged line) the virtual actual image $AB_I$ of the shelf compartment 15 occupied according to FIG. 6a, which is obtained on the basis of the ascertained storage depths. Furthermore, the target image $AB_S$ of the occupation of the shelf compartment shown in FIG. 2a is illustrated in FIG. 6b (as a dotted line).

Based on analysis of the comparison of target image/ actual image, it is determined that the medication packages 31, 33 are shifted or pivoted. The analysis does not permit unambiguous conclusions about the medication package 30 located in the same row of packages as a result of the pivoting or shifting of the medication package 31.

The packages cannot be retrieved without problems, without the hazard existing that surrounding medication packages located on the theoretically provided storage space will also possibly be shifted. Specifically, it cannot be unambiguously detected in the actual image where the medication packages 31, 33 end, since the end faces thereof, which are detectable by the sensor, overlap during the detection of the storage depths.

Furthermore, it is determined that the medication packages 31, 33 (and also 30) can no longer be unambiguously assigned to medication packages which are theoretically present in the inventory. For example, it is not possible to exclude that the medication packages 31, 33 were confused during the manual retrieval, etc.

In such a case, it is checked which adjacent medication packages can be assigned to theoretically present medication packages (medication packages 29, 34 here). All or at least a part of the medication packages which can be assigned to those theoretically present, are then retrieved or relocated and then the remaining medication packages are retrieved. At this point in time, the shelf compartment is substantially cleared out around the imperfection and the gripping device can separate the medication packages as needed until the medication packages can be retrieved using the gripping device; the storage depth and therefore an actual image of the shelf compartment (or of the affected section) may possibly still be ascertained once again for this purpose for the remaining and possibly separated medication packages. After retrieval of the medication packages, they are identified and then stored again.

What is claimed is:

1. A method for detecting incorrect storage of medication packages in a pharmacy order-picking device, the method comprising:
   providing the pharmacy order-picking device, the device comprising:
      at least one row of shelves, each having a plurality of shelf bases extending in a horizontal direction and a plurality of shelf walls extending in a vertical direction, wherein the plurality of shelf bases and the plurality of shelf walls form a plurality of shelf compartments,
      at least one operating device, which is movable in the horizontal direction and in the vertical direction on a front side of the plurality of shelf compartments, wherein the operating device comprises:
         a gripping device for placing and/or retrieving medication packages on or from the shelf bases,
         a sensor, and
         a control unit coupled to the operating device,
   identifying, from the plurality of shelf compartments, a shelf compartment marked as having incorrect storage of medication packages,
   scanning, using the sensor of the operating device, the identified shelf compartment from a front side of the identified shelf compartment in the horizontal direction,
   determining a depth of the identified shelf compartment based on the scanning,
   generating a first actual depth image of the identified shelf compartment based on the determined depth of the identified shelf compartment,
   comparing the first actual depth image to a target depth image of the identified shelf compartment, and
   analyzing deviations between the target depth image and the first actual depth image.

2. The method of claim 1, wherein the shelf compartment is marked as having the incorrect storage of the medication packages by a user, or
   the shelf compartment is marked as having the incorrect storage of the medication packages automatically after one or more medication packages are manually retrieved from the shelf compartment.

3. The method of claim 1, wherein the shelf compartment is marked as having incorrect storage when the shelf compartment is affected during a disturbance of the pharmacy order-picking device.

4. The method of claim 1, wherein the target depth image is generated on the basis of a target occupation of the shelf compartment.

5. The method of claim 1, wherein the target depth image of the shelf compartment is generated or updated when placing the medication packages in the shelf compartment or when retrieving the medication packages from the shelf compartment, and
   the generated target depth image or the updated target depth image is loaded from a memory of the control unit for the comparison.

6. The method of claim 1, further comprising, if a result of the analysis of the deviations between the target depth image and the first actual depth image indicates that at least one medication package is missing from the shelf compartment, the at least one medication package is removed from a theoretical inventory stored in the control unit.

7. The method of claim 1, further comprising, if a result of the analysis of the deviations between the target depth image and the first actual depth image indicates that at least one medication package, which is not recorded in a theoretical inventory, is stored in the shelf compartment, the at least one medication package is retrieved or identified and stored again.

8. The method of claim 1, further comprising, if a result of the analysis of the deviations between the target image and the first actual image indicates that a medication package is shifted,
   determining, based on the incorrect storage of the medication package, whether the shifted medication package is retrievable using the gripping device, and
   if the shifted medication package is retrievable using the gripping device, retrieving the shifted medication package and storing the shifted medication package again.

9. The method of claim 8, further comprising, if the shifted medication package is not retrievable using the gripping device,
   determining that the shifted medication package can be unambiguously assigned to a theoretically present medication package, and,
   retrieving surrounding medication packages and then retrieving the remaining medication package such that it can be stored again.

10. The method of claim 9, further comprising, determining that the shifted medication package cannot be unambiguously assigned to a theoretically present medication package,
    ascertaining which adjacent medication packages can be assigned to theoretically present medication packages;
    retrieving a set of medication packages which can be assigned to theoretically present medication packages, and
    retrieving remaining medication packages, and storing the remaining medication packages.

11. The method of claim 8, further comprising, if the shifted medication package cannot be retrieved using the gripping device, informing a user accordingly and prompting the user to perform manual retrieval.

12. The method of claim 1, further comprising, after a correction of shelf compartment having incorrect storage,
scanning the identified shelf compartment again in the horizontal direction with the sensor of the operating device, and
determining the depth of the identified shelf compartment at various X positions using the sensor,
generating a second actual depth image of the identified shelf compartment on the basis of the depth of the identified shelf compartment after the correction of the shelf compartment,
comparing the second actual depth image to the target depth image of the identified shelf compartment, and
analyzing deviations between the target depth image and the second actual depth image.

13. A method for detecting incorrect storage of medication packages in a pharmacy order-picking device, the method comprising:
identifying a shelf compartment marked as having incorrect storage of medication packages;
moving an operating device in the pharmacy order-picking device to a predefined shelf position at the identified shelf compartment;
scanning, using a sensor of the operating device, the identified shelf compartment from a front side of the identified shelf compartment along a horizontal direction of the shelf compartment;
determining a storage depth of the identified shelf compartment at a plurality of positions along the identified shelf compartment based on the scanning;
generating an actual depth image of the identified shelf compartment, based on the determined storage depth of the shelf compartment at the plurality of positions along the shelf compartment;
comparing the actual depth image to a target depth image of the shelf compartment; and
determining deviations between the target depth image and the actual depth image based on the comparison.

14. The method of claim 13, wherein identifying the shelf compartment having incorrect storage of medication packages comprises marking, by a user, the shelf compartment as having incorrect storage of medication packages.

15. The method of claim 13, wherein identifying the shelf compartment having incorrect storage of medication packages comprises automatically marking, after a manual retrieval of medication packages, the shelf compartment as having incorrect storage of medication packages.

16. A method for detecting incorrect storage of medication packages in a pharmacy order-picking device, the method comprising:
identifying a shelf compartment having incorrect storage of medication packages;
moving an operating device in the pharmacy order-picking device to a predefined shelf position at the identified shelf compartment;
moving the operating device along a horizontal direction along the shelf compartment;
determining, using the sensor, a storage depth at a plurality of positions along the shelf compartment;
preparing an actual image of the shelf compartment, based on the storage depth at the plurality of positions along the shelf compartment;
comparing the actual image to a target image of the shelf compartment; and
determining deviations between the target image and the actual image based on the comparison,
wherein the target image is prepared or updated when placing and retrieving medication packages in or from the shelf compartment and is loaded from a memory of a control unit.

17. The method of claim 13, further comprising:
determining that a medication package is missing from the shelf compartment based on the deviations between the target depth image and the actual depth image; and
erasing the medication package from a theoretical inventory stored in a control unit.

18. The method of claim 13, further comprising:
determining that a medication package which is not recorded in a theoretical inventory is stored in the shelf compartment;
retrieving the medication package or identifying the medication package; and
storing the medication package.

19. A method for detecting incorrect storage of medication packages in a pharmacy order-picking device, the method comprising:
identifying, from a plurality of shelf compartments, a shelf compartment marked as having incorrect storage of medication packages;
moving a sensor of an operating device along a horizontal direction along the shelf compartment to scan the shelf compartment marked as having incorrect storage of medication packages;
scanning, using the sensor of the operating device, the identified shelf compartment from a front side of the identified shelf compartment in the horizontal direction;
determining, using the sensor, a storage depth of the shelf compartment at a plurality of positions along the shelf compartment;
preparing an actual depth image of the shelf compartment based on the determined storage depth at the plurality of positions along the shelf compartment;
comparing the actual depth image to a target depth image of the shelf compartment; and
determining deviations between the target depth image and the actual depth image based on the comparison.

20. The method of claim 19, further comprising:
determining that a medication package has shifted;
determining whether the shifted medication package is retrievable using a gripping device of the pharmacy order-picking device; and
if the shifted medication package is retrievable, retrieving the shifted medication package and storing the medication package.

* * * * *